United States Patent [19]

Blakely et al.

[11] Patent Number: 5,135,144
[45] Date of Patent: Aug. 4, 1992

[54] INSULATED DRUG SUPPLY POUCH

[75] Inventors: David C. Blakely, Mountain View; Hal Rucker, Redwood City, both of Calif.

[73] Assignee: Eli Lilly and Company, Indianapolis, Ind.

[21] Appl. No.: 574,649

[22] Filed: Aug. 29, 1990

[51] Int. Cl.$^5$ .............................................. A45F 5/00
[52] U.S. Cl. .................... 224/240; 224/245; 224/253; 206/366
[58] Field of Search ............... 224/148, 236, 240, 241, 224/242, 245, 253, 224, 908, 920, 921; 206/316.2, 366, 370, 523; 220/910; 383/43, 93, 95, 110, 113; 62/457.1, 457.2, 457.7

[56] References Cited

U.S. PATENT DOCUMENTS

| | | | |
|---|---|---|---|
| 1,113,590 | 10/1914 | Williamson | 224/252 |
| 2,022,251 | 11/1935 | Malloy et al. | 383/95 X |
| 2,081,930 | 6/1937 | Hoffman | 220/354 |
| 2,321,360 | 6/1943 | Chambers | 224/191 |
| 2,695,646 | 11/1954 | Van Wyk | 383/95 X |
| 3,143,263 | 8/1964 | Farmer | 224/235 |
| 3,158,300 | 11/1964 | Withee | 446/186 |
| 3,910,470 | 10/1975 | Swenson et al. | 224/908 X |
| 3,980,216 | 9/1976 | Nye | 224/209 |
| 4,174,798 | 11/1979 | Pollard | 224/253 |
| 4,330,073 | 5/1982 | Clark | 224/240 X |
| 4,363,433 | 12/1982 | Jaques | 224/253 |
| 4,444,342 | 4/1984 | Powell | 224/252 |
| 4,468,933 | 9/1984 | Christopher | 62/457.1 |
| 4,483,089 | 11/1984 | Johnson | 224/253 X |
| 4,545,414 | 10/1985 | Baum | 224/224 X |
| 4,738,364 | 4/1988 | Yeager | 62/457.1 X |
| 4,757,894 | 7/1988 | Schreckenstein | 224/253 X |
| 4,796,790 | 1/1989 | Hamilton | 224/253 |
| 4,826,073 | 5/1989 | Bruno | 206/366 X |
| 4,836,428 | 6/1989 | Evans et al. | 224/253 |
| 4,923,060 | 5/1990 | Breslau | 206/316.2 |
| 4,923,105 | 5/1990 | Snyder | 224/240 X |
| 4,928,819 | 5/1990 | Jakobsen | 206/316.2 |
| 4,969,554 | 11/1990 | Sawaya | 206/370 |
| 4,976,352 | 12/1990 | Nordstrom | 206/316.2 |

Primary Examiner—Henry J. Recla
Assistant Examiner—Robert M. Fetsuga
Attorney, Agent, or Firm—Robert E. Lee; Leroy Whitaker

[57] ABSTRACT

A belt worn and readily portable medical supply pouch for holding a supply of drug containers in a temperature stable and contamination resistant environment is disclosed. A substantially rectangular housing fabricated from a thick insulating material comprising a bottom, two side panels, a front and a back panel with an open top. A housing thus formed defines a cavity therein for storing a supply of drug cartridges. A protective panel extending across the opening of the housing and angled downward into the cavity is provided to prevent contamination from entering the cavity, while providing access by the hand of a user through the opening and down into the cavity for retrieving one of the drug containers. The housing is covered inside and out by a water-proof and contamination-resistant nylon material. Two belt loop members are affixed to the back panel of the housing for attaching the pouch to the waist belt of a user. An internal pocket inside the cavity of the housing is provided for containing a heating element for heating the interior cavity. An outside auxiliary pocket is attached to the outside surface of the front panel for storing items not requiring an insulated and contamination free environment.

11 Claims, 2 Drawing Sheets

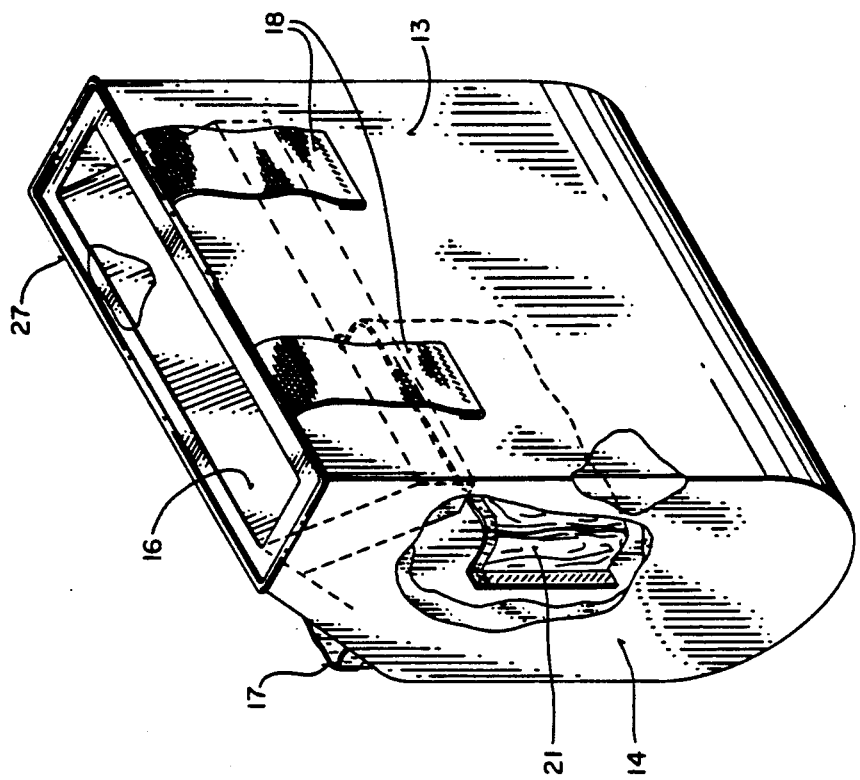
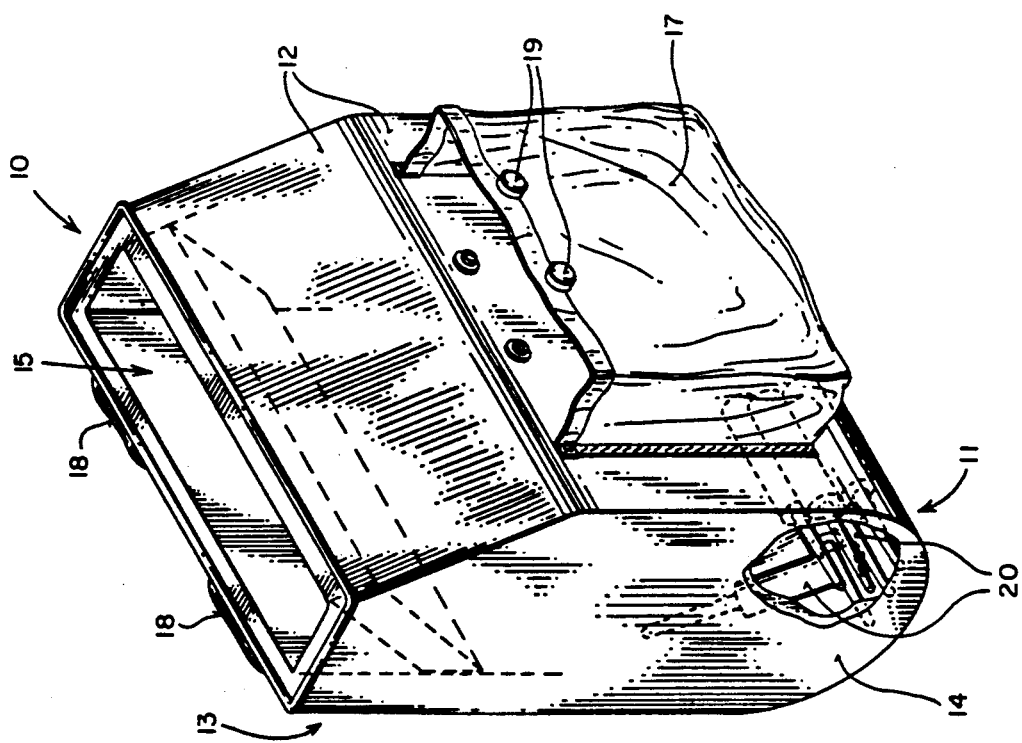

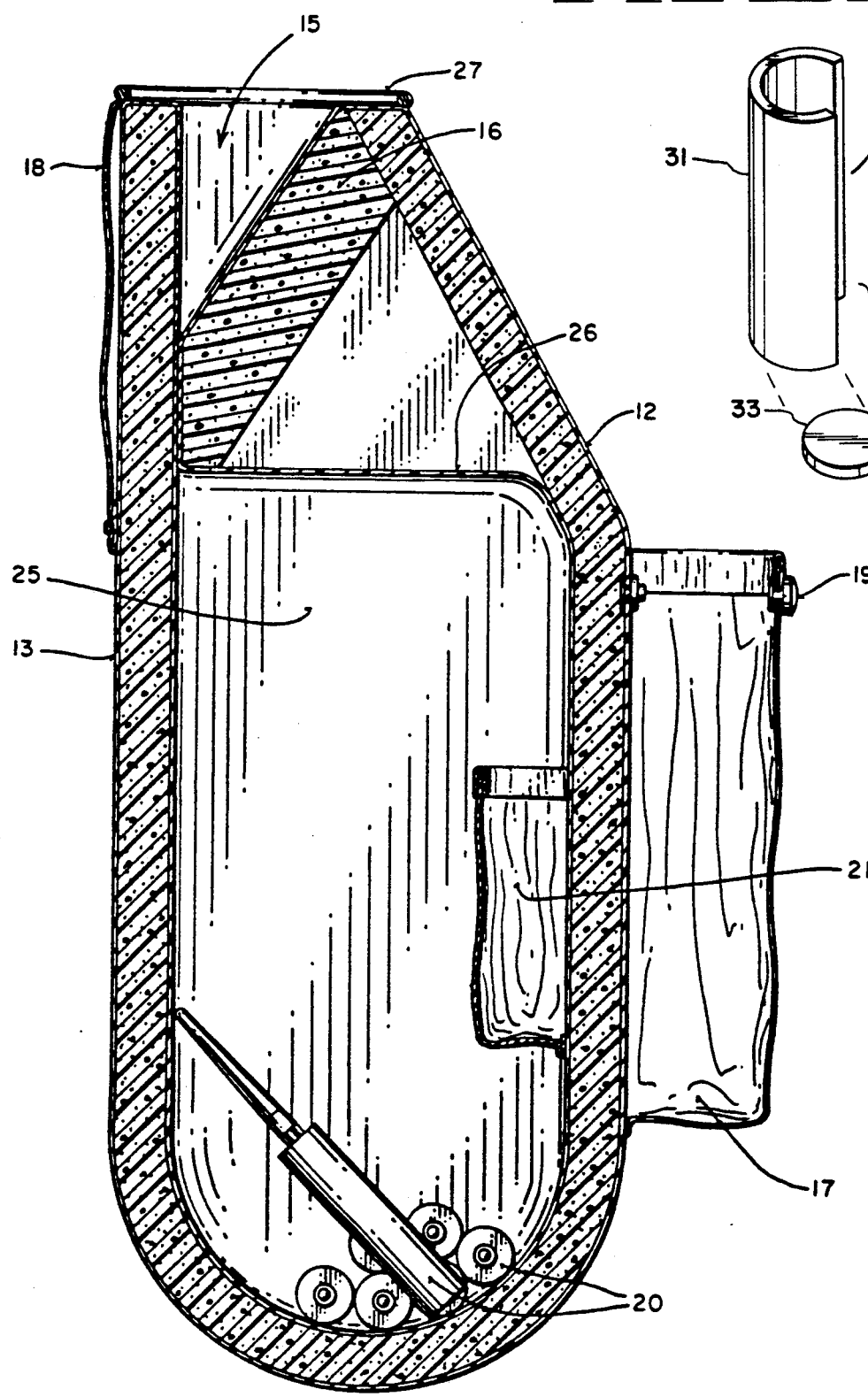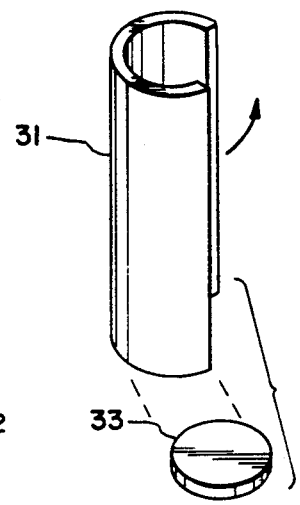

INSULATED DRUG SUPPLY POUCH

BACKGROUND OF THE INVENTION (1) Field of the Invention

The present invention relates to belt-mounted supply pouches. More specifically, the present invention relates to an environmentally protected, belt-mounted supply pouch used for holding drug cartridges in a temperature insulated and contamination resistant environment.

(2) Prior Art

Medical personnel are sometimes required to administer subcutaneous injections to patients in the field or outside the confines of a medically sterile and temperature controlled clinical environment. Veterinarians are often called upon to administer injections to domestic livestock in barnyards, corrals, or out-buildings. These environments are typically subject to high levels of surface and airborne contaminants such as dirt, animal excrement, animal hair, feed particulate or other forms of contamination. In addition, these environments are subject to weather and temperature extremes. Field injections typically take place year-round in many geographical areas; thus, the field environment in which these injections occur is subject to the extreme cold of the winter months or northern latitudes and the extreme heat of summer months or southern latitudes.

The need for a drug injection system for use in the field is increasingly more important. In general, such systems employ a delivery means for injecting a drug formulation from a prefilled and disposable cartridge or container. Many drug formulations such as antibiotics, steroids, vitamins, or formulations for increasing milk or meat yield in domestic animals can be administered using these drug delivery systems. One particularly significant formulation is bovine somatotropin (BST) for use as an agent for increasing milk production efficiency of dairy cows. Often these formulations are sensitive to temperature extremes present in the environment in which they are administered. This is true not only because the formulations themselves may be rendered ineffective beyond some temperature threshold, but also because an increase in the viscosity of a particular formulation associated with a decrease in temperature may render the drug delivery system used with the formulation inoperable. An important component lacking in a typical field-use drug delivery system is a means for storing a supply of drug containers in an insulated, contamination resistant and readily portable supply pouch.

Prior art supply pouch designs typically do not provide an insulated cavity; since, most prior art pouches are not oriented toward medical or drug cartridge containment applications. Those prior art pouches including insulation are not designed to be attached to a belt and worn on the waist of the user. The added benefit of a contamination resistant design is not apparent in the prior art. Further, the ability to reach into a covered pouch without opening a cover is not apparent in the prior art. The combination of these features has been particularly difficult to achieve because of the bulky nature of the insulating material and the need for a belt-mounted device to be small, compact, and easily portable.

Thus, a readily portable yet temperature insulated and contamination resistant supply pouch for holding a supply of drug cartridges or containers is needed.

SUMMARY OF THE INVENTION

The preferred embodiment of the present invention includes a belt-worn medical supply pouch used for holding a supply of drug containers in a cavity insulated from contaminants and temperature extremes. The medical supply pouch comprises a substantially rectangular housing fabricated from a thick insulating material and covered with a water-proof fabric. The supply pouch housing comprises a front and back panel, two side panels, a bottom and an open top. The bottom, side, front and back panels are affixed at edges, thus defining a housing with an interior region or cavity of the pouch. Extending across the top opening from one side panel to the other side panel is a protective panel angled downward toward the interior cavity of the pouch. The protective panel restricts the entry of contaminants into the interior of the pouch while allowing a user of the pouch to conveniently and repeatedly insert a hand into the pouch to retrieve a drug cartridge contained therein. Two belt loop members are affixed to the back panel of the pouch. A user of the pouch may wear the pouch on his/her hip by passing a belt through the two belt members affixed to the pouch, thus attaching the device to the waist of an individual using the supply pouch. A rectangular auxiliary pocket affixed on three sides to the front panel of the pouch housing is included with a closure flap extending across and over the open top of the auxiliary pocket. The supply pouch further includes a small heating element containment pocket affixed to an interior wall inside the cavity of the pouch. The containment pocket is used for holding a chemical or electrical heating element for heating the interior cavity of the supply pouch. The insulating material forming the panels of the medical supply pouch are covered with a water proof nylon or other material designed to be resistant to moisture and contaminants.

BRIEF DESCRIPTION OF THE DRAWINGS

FIG. 1 is a frontal elevation view of the medical supply pouch of the present invention showing the front panel, the top and a side panel.

FIG. 2 is a rear elevation view of the supply pouch showing the back panel, the top and a side panel.

FIG. 3 is a section view showing the internal cavity of the pouch from a side view.

FIG. 4 is a perspective, schematic view showing an alternate embodiment of a portion of the medical supply pouch of the present invention.

DETAILED DESCRIPTION OF THE PREFERRED EMBODIMENT

In the preferred embodiments, described and illustrated in the drawings provided herein, the present invention disclosed provides a readily portable means for holding a supply of drug containers in a temperature-stable and contamination resistant environment.

Referring to FIG. 1, a preferred embodiment of the supply pouch 10 of the present invention is illustrated. The medical supply pouch 10 is shown to comprise a generally rectangular housing formed from a front panel 12 and a back panel 13 connected by or bonded with side panels 14 and bottom 11. Each of the panels comprising said housing are formed from an insulating material approximately ½ inch thick and cut at substantially perpendicular edges. The insulating material is a commonly available synthetic foam or styrofoam material with an insulating factor suitable for outdoor use.

In a first alternative embodiment, the front panel 12, bottom 11 and back panel 13 are all formed from a single piece of insulating material. In this embodiment, a generally rectangular piece of insulating material is cut and folded to form a U-shaped front and back panel with a rounded bottom. Side panels 14 are two additional pieces of insulating material cut to conform to the U-shaped edges defined by the bottom, front and back panels. The side panels 14 are connected or glued to the edges of the bottom, front and back panels with a suitable and commonly available adhesive capable of bonding synthetic foam or rubber material and resilient to moisture and temperature extremes. In an alternative embodiment, side panels 14 may be connected to the bottom, front and back panels by sewing the edges of side panels 14 to front panel 12, back panel 13 and bottom 11. In either equivalent manner, side panels 14 are permanently connected to front panel 12, back panel 13 and bottom 11 to form the housing of the present invention.

In a second alternative embodiment, front panel 12, back panel 13 and bottom 11 may be cut as three separate pieces of insulating material instead of the single piece as described in the first alternative embodiment. These three substantially rectangular pieces are cut from a stock of insulating material and bonded or connected at the edges, along with side panels 14, to form a substantially rectangular housing equivalent to the housing described in the first alternative embodiment. In both the first and second alternative embodiments, panels may be connected at the edges using a suitable adhesive compound or by sewing the edges together as described above.

In a third alternative embodiment, the housing 10 depicted in FIG. 1 is formed from a single molded piece of insulating material. In this equivalent embodiment, the panels forming the housing of the supply pouch are formed from a unitary construction molding process wherein each of the panels comprising the housing are integrally connected at edges in a single manufacturing process. Techniques for creating a unitary construction housing of this type are well known in the art.

Using any of the three equivalent alternative embodiments described above, a generally rectangular housing open at one end and having a bottom, an upright front and back panel, and two side panels is described. The housing thus described defines an opening 15 and an internal cavity 25 used for storing a supply of drug cartridges. In order to reduce the dimension of aperture 15, a portion of front panel 12 is angularly inclined or tapered toward rear panel 13. One edge of side panels 14 is tapered in corresponding fashion with the incline of front panel 12 in order to achieve closure of the housing without overextended sides. The reduced opening 15 is less vulnerable to contamination entering the pouch from the top.

In a fourth alternative embodiment, front panel 12, back panel 13 and side panels 14 are formed from a single rectangular piece of insulating material 31 in FIG. 4 that is rolled into a cylindrical shape open at both ends. A bottom panel 33 may then be connected to the edges of one end of the cylindrical shape to form a housing open at one end with a side panel and a bottom panel.

Referring again to FIGS. 1 and 3, top opening 15 is formed widely enough to allow access for the hand of a user of the supply pouch. Opening 15 is also long enough to allow the removal of a drug cartridge 20 contained within the cavity 25 of the housing 10. In order to prevent foreign material or contamination from entering opening 15 and dropping into cavity 25 inside the housing, a protective panel 16 is provided as shown in FIGS. 2 and 3. Protective panel 16 is fabricated from the same insulating material comprising the other panels forming the housing. Protective panel 16 is also a substantially rectangular piece of insulating material positioned inside opening 15 and connected to the interior surface of front panel 12. A well-known adhesive or bonding agent is used to connect an upper edge of protective panel 16 to the interior surface of front panel 12. Protective panel 16 is angled downward into the housing cavity and inclined toward the interior surface of back panel 13. This configuration facilitates access to the interior cavity 25. Protective panel 16 is cut to a dimension allowing the lower edge of protective panel 16 to make contact with the interior surface of back panel 13. The incline or tapering of the portion of front panel 12 which reduces the size of opening 15 also serves to reduce the size of protective panel 16 necessary to protect opening 15. Protective panel 16 is typically not bonded to the interior surface of back panel 13. Rather, one or more edges of protective panel 16 flexibly abut or nearly abut back panel 13. Protective panel 16 may also be connected to the interior surfaces of side panels 14 at 35.

By virtue of the natural elasticity and flexibility of the insulating material from which protective panel 16 and the other housing panels are made, a user of the pouch will flexibly deflect protective panel 16 away from the interior of back panel 13 when inserting his/her hand into opening 15 and down into housing cavity 25. When the user removes his/her hand from housing cavity 25, the natural elastic action of the insulating material again acts to urge the return of protective panel 16 to a stable position in contact with or abutting the interior surface of back panel 13 as shown in FIG. 3. The incline of the portion of front panel 12 which reduces the size of opening 15 also minimizes the degree of deflection necessary for protective panel 16 while the cavity 25 is being accessed. Minimizing the degree of deflection of the protective panel 16 tends to increase the number of times the protective panel 16 can be deflected before the elastic nature of the material wears out.

There is no need for any hinge or spring loaded mechanisms in the preferred embodiment of the present invention. Thus, the action of retrieving a cartridge from the pouch can be performed in one fluid motion without the need to manipulate a cover flap or opening mechanism. The protective panel 16 always covers opening 15 except when a hand or other object is in the process of accessing the interior cavity 25. Thus, the protective panel 16 provides a maximum of protection from contamination with a minimum of user manipulation. The lack of user manipulation required to access the pouch facilitates the quick retrieval of drug cartridges, thereby increasing the number of injections that can be administered in a given time period.

In a first alternative embodiment, the entire outer surfaces of the housing and protective panel 16 are covered with a nylon pack cloth material with a waterproof urethane coating. The nylon coating acts to protect the pouch from moisture and contamination and to provide an additional level of insulation for the drug containers 20 contained within cavity 25. Other equivalent water-proof and wear-resistent coating materials may also be used, such as a treated canvas or suitable synthetic material. The interior surface of the panels forming the housing are also lined with a water-proof nylon material. As shown in FIG. 3, this interior lining 26 extends throughout the surfaces forming cavity 25 and connects with the material covering the upper surface of protective panel 16. Extending entirely around opening 15 at the top of the housing 10, the exterior protective layer is connected to the interior lining at a seam 27 extending around the opening 15. The seam 27 thus connecting the interior and exterior protective layers is formed using a standard and well known sewn seam with piping added for a better weather proof seal.

In a second alternative embodiment, the housing does not require a weather proof exterior or interior protective layer. Rather, the insulating material comprising panels of the pouch is itself a water-proof and wear-resistent material. These insulating materials such as a synthetic foam or styrofoam material may not require a water-proof exterior layer.

The present invention is designed to be worn on a waist belt of a user of the supply pouch. In order to provide this means of convenient use and portability, attaching means or belt loops 18 are provided as shown in FIGS. 2 and 3. This attaching means 18 comprises two rectangular strips of nylon material affixed to the exterior side of back panel 13. Belt loops 18 are attached to back panel 13 at the upper and lower edges of the strips only. This provides an opening between the interior side of the belt loop and the exterior side of back panel 13 through which a belt or strap may be slideably inserted. Belt loops 18 may be attached to back panel 13 at the upper and lower point using a sewn down stitch or a suitable adhesive bonding agent. The material from which belt loops 18 are made and the technique used to affix belt loops 18 to back panel 13 must produce belt loops of sufficient strength to support a fully loaded supply pouch as it hangs from the belt of a user.

Referring to FIGS. 1 and 3, a small pocket 21 is attached to the interior wall of front panel 12 and contained within cavity 25. Pocket 21 is used for holding a small heating element, such as a chemically active or battery operated heater for the purpose of heating the interior cavity 25 of housing 10. In the preferred embodiment, pocket 21 is formed from a substantially rectangular piece of nylon or other suitable material sewn or glued around three sides to the interior lining of front panel 12. Three sides of the rectangular pocket thus attached leaves the top side open and accessible for inserting a small heating element into the pocket. Methods for sewing or gluing pocket 21 to the interior lining in this manner are well known in the art.

In an alternative embodiment, heating containment means 21 may be implemented as a horizontal loop of material attached to the interior lining of front panel 12. Two ends of the loop are attached leaving the surface between the ends open and accessible for slideably placing a heating element therein. In this embodiment, the heating element must be configured in a way to prevent the heating element from sliding all the way through the containment loop.

Whether the heating element containment means is implemented as pocket 21, a horizontal loop, or other means, the heating element containment means provides the desirable features of holding a heating element up and away from drug cartridges 20 while still providing easy access for a user to insert a hand into opening 15 down into cavity 25 in order to retrieve one of the drug cartridges 20. Also, by inserting a hand into opening 15 and into cavity 25, a heating element may be installed into pocket 21 or removed therefrom as necessary.

Referring again to FIGS. 1 and 3, an external auxiliary pocket 17 is affixed to the outside surface of front panel 12. In order to provide a storage means for items not requiring the insulated and contamination resistant environment inside the housing, auxiliary pocket 17 is provided. In the preferred embodiment, pocket 17 is fabricated from a substantially rectangular piece of nylon or other suitable material sturdy enough to withstand the more severe environmental conditions outside the pouch. Pocket 17 is sewn or glued around three sides onto the outside surface of front panel 12. A pocket thus attached provides an opening at the top for access to items stored therein. A pair of water-resistant snaps 19 are attached to the open edge of pocket 19 in order to provide closure of the pocket against snap receiving and locking means attached to the outer surface of front panel 12. Snapping means (i.e. snap buttons) and a method for attaching same to pocket 17 and front panel 12 are well known in the art.

Thus, a belt worn medical supply pouch used for holding a supply of drug containers in a cavity insulated from contaminants and temperature extremes is disclosed.

Although this invention has been shown in relation to particular embodiments, it should not be considered so limited. Rather, it is limited only by the appended claims.

What is claimed is:

1. An insulated drug supply pouch for holding a supply of drug containers comprising:
    a bottom with an upright front panel and back panel formed from a single piece of insulating material;
    side panels connected to said front and back panels of said bottom, said side panels and said bottom forming a generally rectangular housing open at one end and defining a cavity therein;
    a protective panel fixedly connected to said housing and covering said open end of said housing, said protective panel formed from an elastic material allowing access to said cavity by a hand, said protective panel being fixed to the interior side of said front panel and inclined downward towards said back panel, said protective panel being deflectible away from said back panel into the housing cavity by said hand, said protective panel returning to its original position after said hand is removed; and
    attaching means connected to said back panel for attaching said pouch to the waist belt of a wearer.

2. The pouch as claimed in claim 1 wherein said protective panel is affixed only to said front panel and said side panels.

3. An insulated and portable pouch for holding a supply of drug containers comprising:
    a generally rectangular housing open at one end and having an upright front and back panel joined by a bottom and side panels in a unitary construction, said panels fabricated from insulating material and integrally connected to form a housing with a cavity therein;
    a protective panel connected to said housing and covering said open end of said housing, said protective panel flexibly abutting said side and back panels, said protective panel flexibly composed to allow access to said cavity by a hand through said open end, said protective panel being fixed to the interior side of said front panel and inclined downward towards said back panel, said protective panel being deflectible away from said back panel into the housing cavity by said hand, said protective panel returning to its original position after said hand is removed; and attaching means connected to said back panel for attaching said housing to the waist belt of a wearer.

4. The pouch as claimed in claim 3 wherein said front panel, said back panel, and said bottom are fabricated from a single piece of insulating material.

5. The pouch as claimed in claims 1 or 3 further including an auxiliary pocket affixed to the outer side of one of said panels, said auxiliary pocket having an open upper side allowing access to the interior of said pocket.

6. The pouch as claimed in claims 1 or 3 further including a heating element pocket affixed to the inner side of one of said panels, said heating element pocket adapted to hold a heating element for heating said cavity.

7. The pouch as claimed in claims 1 or 3 wherein said housing is covered with a water-proof fabric.

8. The pouch as claimed in claims 1 or 3 further including an auxiliary pocket affixed to the outer side of one of said panels, said auxiliary pocket having an open upper side allowing access to the interior of said pocket, said open upper side having closure snaps affixed thereto for closing said open upper side using cooperating snap locking means affixed to the exterior side of said panel.

9. The pouch as claimed in claims 1 or 3 wherein said protective panel is affixed only to said front panel.

10. The pouch as claimed in claims 1 or 3 wherein said housing is tapered to reduce the size of said open end of said housing.

11. The pouch as claimed in claims 1 or 3 wherein said protective panel is fabricated from a flexible material which deflects away from said open end of said housing while a hand is inserted into said cavity and returns to a position covering said open end when said hand is removed.

* * * * *